United States Patent [19]

Varadaraj et al.

[11] Patent Number: 5,672,739

[45] Date of Patent: Sep. 30, 1997

[54] CLASS OF THREE TAIL SURFACTANTS LAW388

[75] Inventors: Ramesh Varadaraj, Flemington; Max Leo Robbins, South Orange; Cornelius Hendrick Brons, Washington, all of N.J.

[73] Assignee: Exxon Research & Engineering Company, Florham Park, N.J.

[21] Appl. No.: 678,837

[22] Filed: Jul. 12, 1996

[51] Int. Cl.[6] .................................................. C07C 309/04
[52] U.S. Cl. ........................................... 562/106; 562/109
[58] Field of Search ........................................ 562/109, 106

[56] References Cited

FOREIGN PATENT DOCUMENTS 61-271339  12/1986  Japan .

OTHER PUBLICATIONS

Howes, et al., Xenobiotica, 17(6), 709–23 1987.

*Primary Examiner*—Joseph Conrad
*Attorney, Agent, or Firm*—Joseph J. Dvorak

[57] ABSTRACT

The present invention comprises a novel composition of matter having the general formula:

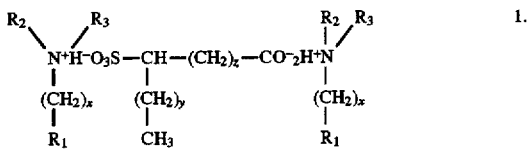

wherein $R_1$ is H or an alkoxide of from 5 to about 20 carbon atoms;

x is an integer of from about 8 to 22 when $R_1$=H and from about 2 to 5 when $R_1$ is an alkoxide;

$R_2$ is selected independently from H, $(CH_2CH_2O)_mH$, and $(CH_2CH(CH_3)O)_mH$;

$R_3$ is selected independently from H, $(CH_2CH_2O)_nH$, and $(CH_2CH(CH_3)O)_nH$;

m and n are integers from 1 to 50; and y and z are integers from 2 to 10.

4 Claims, No Drawings

CLASS OF THREE TAIL SURFACTANTS LAW388

FIELD OF THE INVENTION

The present invention relates to novel surfactants with three hydrocarbon chains.

BACKGROUND OF THE INVENTION

Surfactants are amphiphilic molecules that manifest their properties at interfaces, e.g., at air-liquid, liquid-liquid and solid-liquid interfaces. They can be either water or oil soluble and are of considerable commercial importance because of their applications in petrochemical, pharmaceutical and soap industries. Generally a surfactant molecule is characterized by the presence of a hydrophobic group e.g., a long chain hydrocarbon (tail) attached to a hydrophilic group (head). The hydrophilic head group can be an anionic, cationic or non-ionic group and surfactants are typically classified according to the type of head group.

The vast majority of synthetic surfactants known in the art are molecules with one long hydrocarbon chain attached to one head group. Variations reported in the art include branched hydrocarbon chains and fluorocarbon chains as tails. Surfactant molecules with three hydrocarbon chains attached to one or many head groups are relatively rare.

Also, as is known the impact a surfactant has on a given system is a function of a number of different properties including how the surfactant molecules are oriented at the interfaces in the system, the shape of micelles formed by the surfactant and the like.

Thus, the effectiveness of a given surfactant is not always predictable. One measure, however, of the effectiveness of a surfactant is how much it lowers the surface tension of water at its critical micelle concentration. The lower the surface tension at the critical micelle concentration, the more effective the surfactant is.

One object of the present invention is to prepare new surfactants.

Another object of the present invention is to provide more effective surfactants.

SUMMARY OF THE INVENTION

Accordingly, in one embodiment, the present invention comprises a novel composition of matter having the general formula:

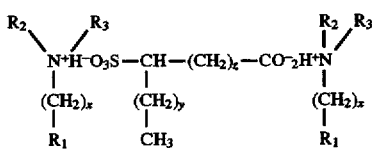

wherein $R_1$ is H or an alkoxide of from 5 to about 20 carbon atoms;

x is an integer of from about 8 to 22 when $R_1$=H and from about 2 to 5 when $R_1$ is an alkoxide;

$R_2$ is selected independently from H, $(CH_2CH_2O)_mH$, and $(CH_2CH(CH_3)O)_mH$;

$R_3$ is selected independently from H, $(CH_2CH_2O)_nH$, and $(CH_2CH(CH_3)O)_nH$;

m and n are integers from 1 to 50; and y and z are integers from 2 to 10.

DETAILED DESCRIPTION OF THE INVENTION

The surfactant compositions of the present invention have two heads, a spacer group separating the heads and three tails. The surfactant is best represented by the general formula:

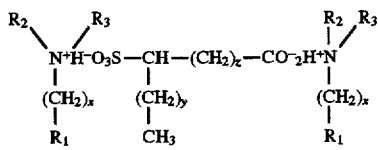

The compounds of the present invention are prepared by neutralization of one mole in a di acid of the formula

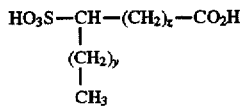

wherein z and y are as previously defined with two moles of an amine or mixture of amines having the formula

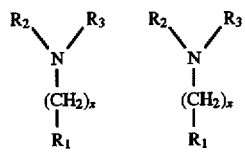

wherein $R_1$, $R_2$, $R_3$ and x are as previously defined.

The neutralization is preferably carried out neat, i.e., by addition of the amine to the acid with mixing in the temperature range of 20° C. to 80° C. Optionally, hydrocarbon diluents such as toluene and the like may also be employed in the neutralization reaction.

The effectiveness of a surfactant of the present invention is demonstrated in the example which follows.

EXAMPLE 1

A three tail surfactant of Formula 1 with $R_1$=H; x=18; $R_2$=$(CH_2CH_2O)_mH$ and $R_3$=$(CH_2CH_2O)_nH$; m+n=10; y=7; and z=8 was synthesized by addition of two moles of octadecyl amine decaethoxylate to one mole of sulfonated oleic acid with mixing at 80° C. Upon cooling the reaction product is a waxy solid at room temperature.

The surfactant character of the reaction product, i.e., the surface tension at the air-water interface was established using static tensiometry by the Wilhelmy plate method. The decrease in air-water surface tension as a function of surfactant concentration was determined and found to decrease from 72 dynes/cm at a concentration of $10^{-7}$ molar to about 36 dynes/cm at a $10^{-5}$ molar solution demonstrating that the composition of the invention is an excellent surfactant. Indeed, as can be seen in Table 1 the product of Example 1 provides a lower water surface tension at its critical micelle concentration (CMC) than the individual components listed in the Table.

TABLE 1

| Compound | Surface Tension (dynes/cm) @ CMC |
|---|---|
| Example 1 | 36.5 |
| Sodium Salt of Sulfonated Oleic Acid | 52.5 |
| Octa decyl amine Decaethoxylate | 40.2 |

What is claimed is:

1. A composition of matter having the general formula:

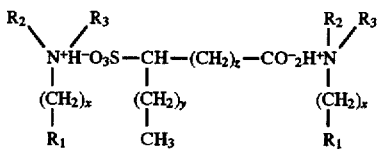

wherein $R_1$ is H or an alkoxide of from 5 to about 20 carbon atoms;

x is an integer of from about 8 to 22 when $R_1$=H and from about 2 to 5 when $R_1$ is an alkoxide $R_2$ is selected independently from H, $(CH_2CH_2O)_mH$, and $(CH_2CH(CH_3)O)_mH$ $R_3$ is selected independently from H, $(CH_2CH_2O)_nH$, and $(CH_2CH(CH_3)O)_nH$;

m and n are integers from 1 to 50; y and z are integers from 2 to 10.

2. The composition of claim 1 wherein $R_2$=$(CH_2CH_2O)_mH$, $R_3$=$(CH_2CH_2O)_nH$; m+n=10; z=8 and x=18.

3. The composition of claim 2 wherein y=7.

4. The composition of claim 2 wherein y=17.

* * * * *